United States Patent
Pinel et al.

(10) Patent No.: US 9,475,742 B2
(45) Date of Patent: Oct. 25, 2016

(54) GLYCEROL CONVERSION BY HETEROGENEOUS CATALYSIS

(71) Applicants: Catherine Pinel, Lyons (FR); Florian Auneau, Cran Gevrier (FR); Nicolas Villandier, Couzeix (FR); Michele Besson, Les Echets (FR); Laurent Djakovitch, Villeurbanne (FR)

(72) Inventors: Catherine Pinel, Lyons (FR); Florian Auneau, Cran Gevrier (FR); Nicolas Villandier, Couzeix (FR); Michele Besson, Les Echets (FR); Laurent Djakovitch, Villeurbanne (FR)

( * ) Notice: Subject to any disclaimer, the term of this patent is extended or adjusted under 35 U.S.C. 154(b) by 0 days.

(21) Appl. No.: 14/653,156

(22) PCT Filed: Dec. 5, 2013

(86) PCT No.: PCT/IB2013/060679
§ 371 (c)(1),
(2) Date: Jun. 17, 2015

(87) PCT Pub. No.: WO2014/097040
PCT Pub. Date: Jun. 26, 2014

(65) Prior Publication Data
US 2015/0336870 A1 Nov. 26, 2015

(30) Foreign Application Priority Data
Dec. 19, 2012 (FR) .................................. 12 62348

(51) Int. Cl.
C07C 51/00 (2006.01)
C07C 29/00 (2006.01)
C07C 29/60 (2006.01)
C07C 51/295 (2006.01)

(52) U.S. Cl.
CPC ............. *C07C 29/60* (2013.01); *C07C 51/295* (2013.01)

(58) Field of Classification Search
CPC .......................... C07C 51/295; C07C 29/60
USPC ......................................................... 562/538
See application file for complete search history.

(56) References Cited

U.S. PATENT DOCUMENTS
2012/0253067 A1 10/2012 Chaudhari et al.

FOREIGN PATENT DOCUMENTS
CN  101225041  7/2008
CN  101695657  4/2010
EP  0201957   11/1986

OTHER PUBLICATIONS

Written Opinion for PCT Application No. PCT/IB2013/060679 filed May 12, 2013 on behalf of Novance. Mailed Mar. 18, 2014. French original and English translation.
Pavel Korovchenko et al. "Oxidation of primary alcohols with air on carbon-supported platinum catalysts for the synthesis of aldehydes or acids" Catalysis Today, 121 (2007) 13-21.
Yohei Kusunoki et al. "Highly active metal-acid bifunctional catalyst system for hydrogenolysis of glycerol under mild reaction conditions" Catalysis Communications 6 (2005) 645-649.
C. Montassier et al. "Transformation de polyols par catalyse hétérogène en phase liquid sur les métaux" Bulletin De La Société Chimique De France. 1989,No. 2, 148-155.
International Search Report mailed on Mar. 18, 2014 for PCT/IB2013/060679 filed on Dec. 5, 2013 in the name of Oleon et al.
Jeroen ten Dam et al. "Tuning selectivity of Pt/CaCO$_3$ in glycerol hydrogenolysis A Design of Experiments approach" Catalysis Communications, Elsevier Science, Amsterdam, NL, vol. 13, No. 1, Jun. 6.
Yihong Shen et al. "Efficient synthesis of lactic acid by aerobic oxidation of glycerol on Au—Pt/TiO$_2$ catalysts" Chemistry—A European Journal, Wiley-V C H Verlag GmbH & Co. KGAA, Weinheim, DE, vol. 16, No. 25, Jan. 2010, pp. 7368-7371, XP009146561.

*Primary Examiner* — Sikarl Witherspoon
(74) *Attorney, Agent, or Firm* — Steinfl & Bruno LLP

(57) ABSTRACT

A method for preparing lactic acid is described, having a step of converting glycerol in the presence of a platinum-based heterogeneous catalyst on a zirconia-based support, in basic medium under inert atmosphere.

16 Claims, 4 Drawing Sheets

GLYCEROL CONVERSION BY HETEROGENEOUS CATALYSIS

CROSS REFERENCE TO RELATED APPLICATIONS

The present application is the U.S. national stage of International Patent Application PCT/IB2013/060679 filed on Dec. 5, 2013 which, in turn, claims priority to French Patent Application 1262348 filed on Dec. 19, 2012.

This invention relates to the technical field of organic synthesis by heterogeneous catalysis and more particularly to the conversion of glycerol into lactic acid.

This type of catalysis is generally known on solid supports such as activated carbon and using metals or alloys such as rhodium, iridium, platinum or a gold/platinum alloy. For example, the synthesis of lactic acid from glycerol has been described in Y. Shen et al. *Chem. Eur. J.* I 2010, 16.7368. This synthesis, conducted at 90° C. under 1 bar of $O_2$ in the presence of a bimetallic Au—Pt/$TiO_2$ catalyst and 4 molar equivalents of base, can be used to obtain a lactic acid yield of 44%, which rules out the possibility of industrial application. Platinum catalysts on silica are considered inactive for the hydrogenolysis of glycerol (see C. Montassier et al, *Bull. Soc. Chim. Fr.* 1989,2,148) while on carbon catalysts such as those of the patent application US2012/0253067 are generally described as having a lower activity for this reaction (see Y. Kusunoki et al, *Catal. Comm.* 2005, 6, 645).

The invention aims to remedy these disadvantages by providing a method for manufacturing lactic acid at a high yield and under conditions allowing industrial application.

Thus a first embodiment of the invention is the use of a Pt/$ZrO_2$-based catalyst in the presence of glycerol in a basic reaction medium.

According to another embodiment, the invention relates to a method for preparing lactic acid comprising a step of converting glycerol in the presence of a platinum-based heterogeneous catalyst on a zirconia-based support, in basic medium under inert atmosphere. This method is for example implemented by combining, under suitable reaction conditions, a glycerol-based substrate and a catalyst as described above.

The term "-based" means that other elements may be present provided that the majority element by weight is that qualified by this term. "Majority" means more than 50% by weight.

It is however preferred that the metal used as the catalyst should contain more than 75%, more particularly more than 95%, by weight of Pt and/or that the support should be made of more than 75%, more particularly more than 95%, by weight of zirconia $ZrO_2$. Thus the catalyst may advantageously be a platinum on zirconia catalyst.

The method according to the invention is conducted in basic medium. This basic medium may be obtained by adding a base, preferably strong, which may be a Brønsted base, such as sodium hydroxide, an organic base such as DABCO (1,4-diazabicyclo[2.2.2]octane) or a solid base such as a mixed lanthanum magnesium oxide. According to the method of the invention, the basic medium may comprise from 0.5 to 5 molar equivalents of a base with respect to glycerol. The quantity of base may be equimolar but it is advantageous that the basic medium should comprise a slight excess of base, in moles, with respect to glycerol. For example, the basic medium preferably comprises from 1 to 1.2 molar equivalents of a base with respect to glycerol. The base may be added throughout the reaction and/or simply be added in one go at a given time. It is preferred that a given quantity of base should be mixed with the substrate comprising glycerol before being brought into contact with the catalyst. The initial pH may therefore be adjusted, for example to be greater than 12 or 13. The addition of base to maintain the reaction at a given pH, for example greater than 11, may be advantageous. According to one aspect of the invention, the basic medium is obtained by adding NaOH.

According to a particular aspect of the invention, the conversion step is conducted under pressure, for example under pressure of nitrogen, helium or another inert gas, either entirely or partially at a pressure of 5 to 35 bar.

One particularly preferred aspect of the invention is that crude glycerol can be used in the catalysis step. Using crude glycerol, the method avoids or reduces the refining steps required to obtain a pure product, especially when the glycerol is biobased, i.e. obtained from vegetable oils or animal fats and in particular from an oil extracted from oilseeds. Thus, crude glycerol is a product which may contain a certain proportion, for example less than 20%, of substances other than glycerol. Such substances may be water, ash and/or fat residues.

According to another preferred aspect of the invention, the quantity of glycerol used in the conversion step is at least 25% (moles) of the starting materials, preferably at least 50%.

It is also preferred that the reaction should be conducted in the presence of a protic solvent such as water.

The reaction may advantageously be conducted, either entirely or partially, at a temperature from 160° C. to 250° C., preferably from 165° C. to 185° C. such as for example 170° C.±3° C. and/or 180° C.±3° C. The reaction is preferably conducted entirely or partially at a temperature of less than 180° C.

According to another aspect of the invention, the method may also be used to obtain 1,2-propanediol, 1,3-propanediol and/or formic acid.

Advantageously, the method according to the invention exhibits a lactic acid yield greater than 55%, preferably greater than or equal to 60% and in particular greater than 65% or even 70%.

According to another embodiment, the method of the invention implements a platinum-based catalyst on an alumina-based support under reaction conditions similar or identical to those described above.

DESCRIPTION OF THE FIGURES

The invention will be better understood on reading the accompanying figures, which are given solely by way of example and not limiting in any way, in which.

EXAMPLES

Example 1

Figure 1A:
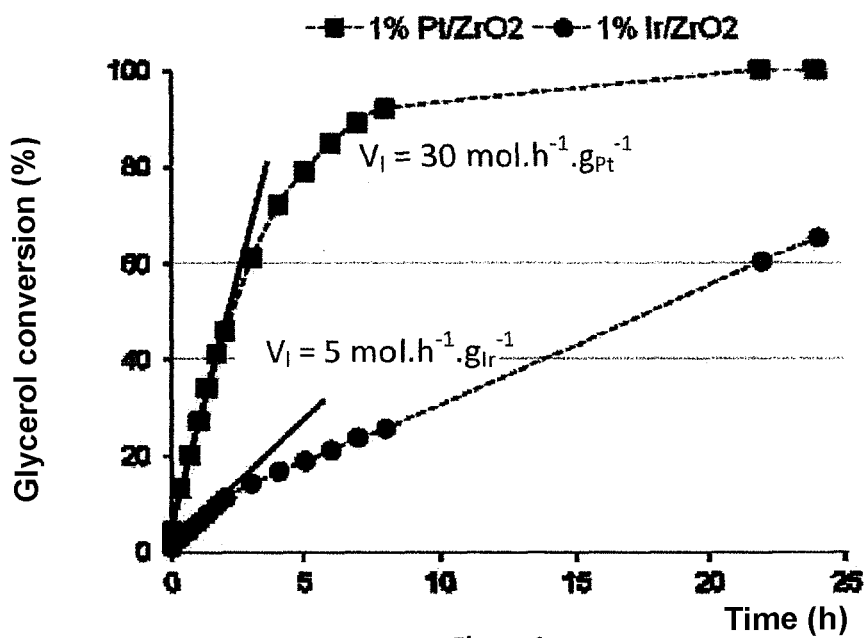
FIG. 1a shows the change in glycerol conversion rate (%) against time (h) and FIG. 1b shows the lactic acid selectivity (%) against the glycerol conversion (%) for 1% Ir/$ZrO_2$ (black circle) and 1% Pt/$ZrO_2$ (black square) catalysts under helium atmosphere according to the method described in Example 1.
Figure 1B:
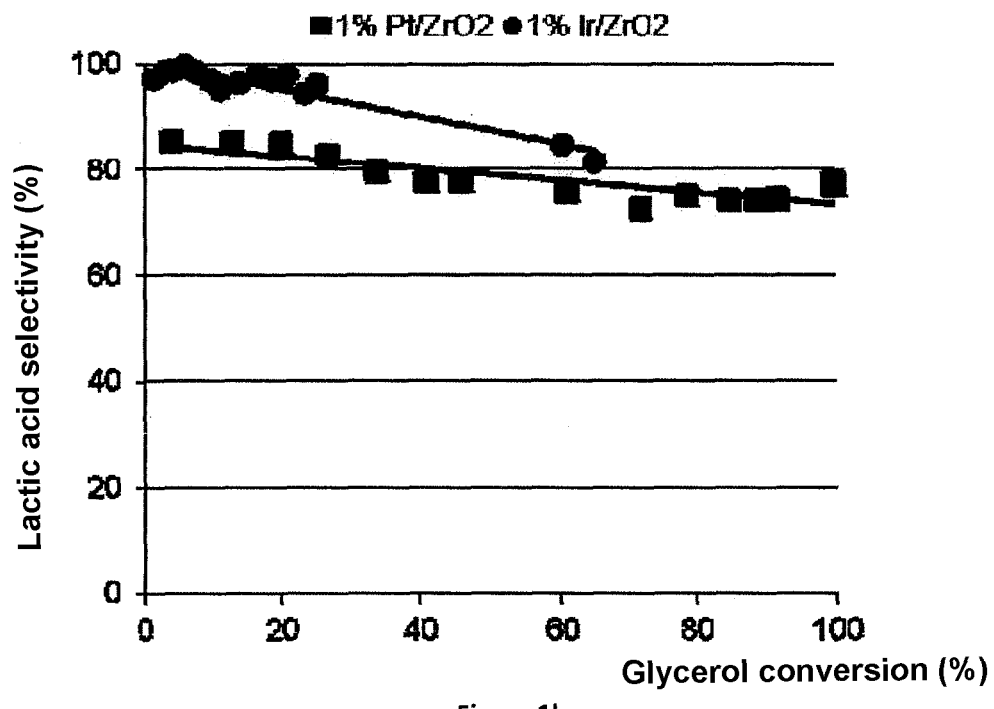

Synthesis of Lactic Acid According to the Method of the Invention and Comparative Study with Another Catalyst on Zirconia Ir/ZrO$_2$ and Pt/ZrO$_2$ (1 wt % of metal) catalysts were prepared by impregnating a ZrO$_2$ support which is a monoclinic zirconia having a BET surface area of 52.9 m$^2$/g, a pore volume of 0.3 mL/g and a pore diameter of between 16 and 60 A (Saint-Gobain, Zirconia NorPro 50 m$^2$/g). The impregnation was carried out with an aqueous solution from IrCl$_3$ and H$_2$PtCl$_6$, 6H$_2$O precursors respectively. After calcination at 600° C. under a stream of air for 12 hours and reduction at 300° C. under H$_2$ for 3 h, catalysts with comparable metal load (about 1 wt %) were obtained. A kinetic study was conducted to compare their activity under reference conditions (100 mL of an aqueous solution of 5% glycerol/NaOH 1M, 180° C., 30 bar inert gas, 500 mg 1% M/ZrO$_2$). The reactants are introduced in a stainless steel autoclave equipped with a Teflon® container and subjected to an initial He pressure of 25 bar (Pf=30 bar). The mixture is stirred constantly at a temperature of 180° C.

Glycerol is converted more rapidly in the presence of the 1% Pt/ZrO$_2$ catalyst than in the presence of the 1% Ir/ZrO$_2$ catalyst. The initial activity of the Pt/ZrO$_2$ catalyst is in fact 6 times greater than that of the Ir/ZrO$_2$ catalyst. After 24 hours of reaction, the conversions reach respectively 100% and 65% (Table 2, entries 1 and 2).

Lactic acid is the majority product observed irrespective of the catalyst used. The formation of lactic acid results in a slight decrease in the pH of the solution. In addition, TOC analysis shows in both cases that 100% of the organic carbon is in solution, which would suggest that any reforming phenomena in aqueous phase only occur to a very slight extent. This result is consistent with the absence of carbon-containing products in the gas phase.

ICP analysis of the reaction medium at end of reaction shows that there is no leaching of either Zr or Pt in solution during the reaction (CPt and CZr<0.1 mg·L$^{-1}$). This observation demonstrates that the production of lactic acid in the presence of Pt/ZrO$_2$ is due to a heterogeneous catalytic method and that it is therefore possible to consider recycling of the catalyst. Under hydrogen atmosphere (Table 1, entry 3), glycerol conversion in the presence of the 1% Pt/ZrO$_2$ catalyst is the same, but the AL yield decreases from 78% to 67%. This decrease is accompanied at the same time by an increase in the 1,2-propanediol yield, which increases from 7% to 23%.

TABLE 1

Comparison of 1% Ir/ZrO$_2$ and 1% Pt/ZrO$_2$ catalysts

| No. | Cat. | pHi | pHf | Conv. (%) | Carbon balance (%)[a] | Yield (%)[b] | | |
|-----|------|-----|-----|-----------|------------------------|--------------|---|---|
|     |      |     |     |           |                        | AL[c] | 1,2-PDO[c] | Others[c] |
| 1 | 1% Pt/ZrO$_2$ | 12.9 | 12.5 | 100 | 100 | 78 | 7 | AF: 7, 1,3-PDO: 2, EG: 2, AA and EtOH: <1 |
| 2 | 1% Ir/ZrO$_2$ | 13.1 | 12.6 | 65 | 100 | 53 | 3 | AF: 2, 1,3-PDO: 1, EG, AA and EtOH: <1 |
| 3 | 1% Pt/ZrO$_2$[d] | 13.1 | 12.6 | 96 | 100 | 67 | 23 | AF: 3, 1,3-PDO: 3, EG: 2, AA and EtOH: <1 |

100 mL 5% glycerol/NaOH 1M, 500 mg catalyst, 25 bar initial He pressure (Pf = 30 bar), 180° C., 24 h.
[a]Determined by TOC analysis.
[b]Determined by HPLC.
[c]AL: lactic acid; 1,2-PDO: 1,2-propanediol; 1,3-PDO: 1,3-propanediol; AA: acetic acid; AF: formic acid; EG: ethylene glycol and EtOH: ethanol.
[d]Reaction conducted under a H$_2$ pressure of 50 bar.

Example 2

Comparative Study of Reactions Synthesizing Lactic Acid from Glycerol in the Presence of a Platinum-Based Catalyst on Various Supports: Pt/ZrO$_2$ and Pt/C The yields and selectivities of the synthesis of lactic acid according to the invention as described in Example 1 were compared with those of a reaction also using a platinum-based heterogeneous catalyst, but on a different support: carbon. The Pt/C catalyst is known to have a very good yield in this reaction.

The Pt/C catalyst used was synthesized according to a method described in the literature P. Korovchenko, C. Donze, P. Gallezot, M. Besson, Catal Today, 2007, 121, 13, from CECA L3S activated carbon having a BET surface area of 900 m$^2$/g. The Pt/C catalyst so obtained has particles of nanometer size, for example from 1 to 3 nm, undetectable by XRD analysis. Synthesis of lactic acid in the presence of Pt/C was conducted under reaction conditions equivalent to the reference conditions of example 1. 100 mL of 5% glycerol, 1.8 equivalent of NaOH, were mixed with 161 mg of Pt/C catalyst at 3%. The mixture was heated to 180° C. under a helium pressure of 30 bar for 25 h.

Figure 2:
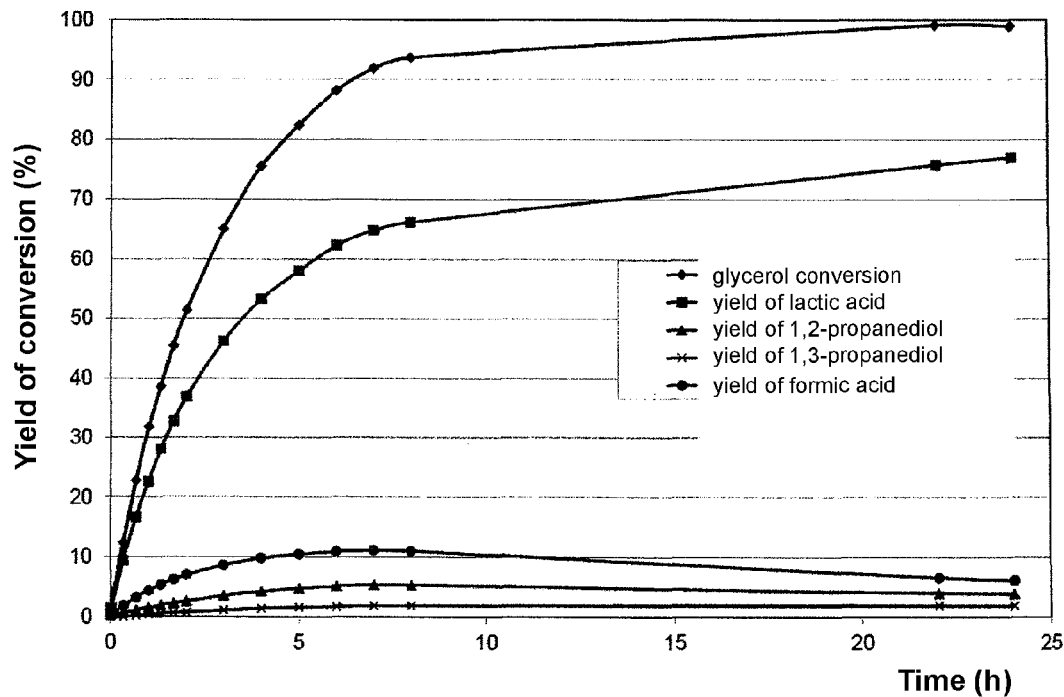
FIGS. 2 and 3 show respectively the change in glycerol conversion and the yields of lactic acid, 1,2-propanediol, 1,3-propanediol and formic acid formed during the reaction conducted in the presence of a platinum/zirconia catalyst (FIG. 2) and in the presence of a platinum/carbon catalyst (FIG. 3).
Figure 3:
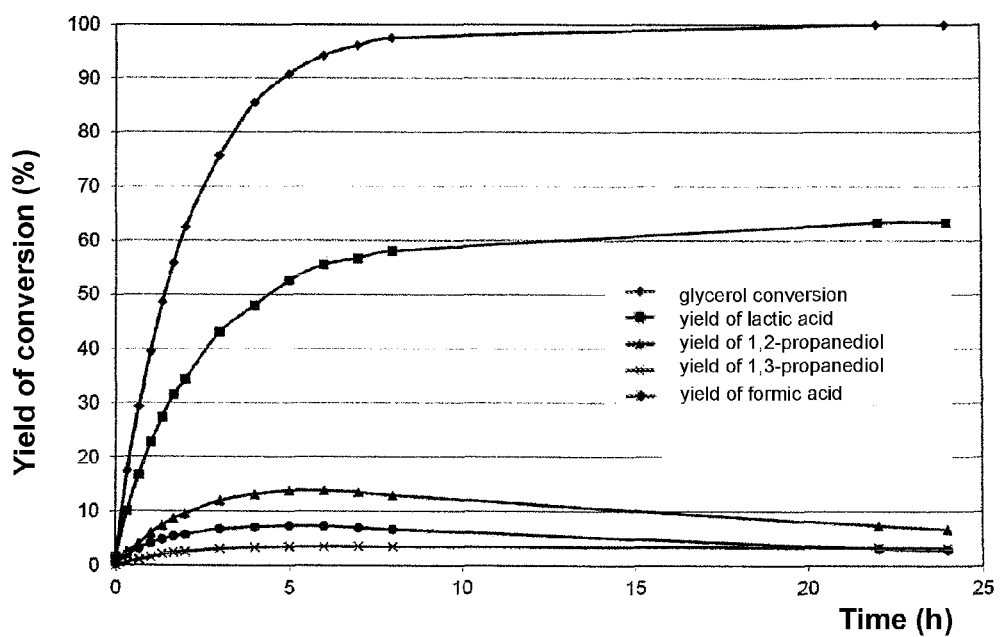

The results of the kinetic study, conducted during the 25 h reaction period, of the glycerol conversion and of the yields of products formed, are shown in FIG. 2 for the reaction according to the invention in the presence of a Pt/ZrO$_2$ catalyst and in FIG. 3 for the reaction with the Pt/C catalyst. The curves show the glycerol conversion rate (black diamond), the lactic acid yield (black square), the formic acid yield (black circle), the 1,2-propanediol yield (black triangle), and the 1,3-propanediol yield (black cross). In these two figures, the time on the abscissa is expressed in hours and the conversion rate or product yield of the reaction on the ordinate is expressed as a %.

We see that the curve (black diamond) in FIG. 2, showing the glycerol conversion approaches 100% in 25 h with values around 98-99% after 23 h of reaction. The curve (black square) showing the lactic acid yield increases exponentially up to a value of nearly 78% after 25 h of reaction. The other reaction products, 1,2-propanediol, 1,3-propanediol and formic acid (curves (black circle), (black triangle) and (black cross)) have low yields, less than 10%.

We see that the curve (black diamond) in FIG. 3 showing the glycerol conversion reaches 100% conversion after 20 h of reaction. However, the curve (black square) showing the lactic acid yield increases exponentially up to a value of nearly 62% at the end of the reaction. The other reaction products, 1,2-propanediol, 1,3-propanediol and formic acid (curves (black circle), (black triangle) and (black cross)) have low yields, less than 15% at 5 h of reaction.

This comparative study shows that the Pt/C catalyst is slightly more active in terms of glycerol conversion than Pt/ZrO$_2$. However, it appears that the selectivity with respect to lactic acid is greater than 10% with a zirconia support than with a carbon support, throughout the progress of the reaction.

Example 3

Figure 4:
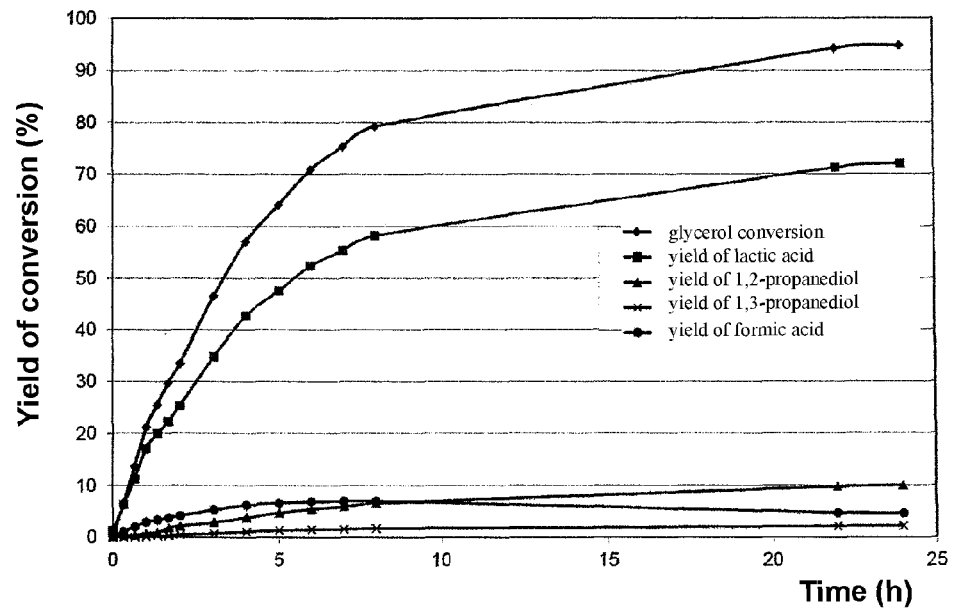
FIGS. 4 and 5 show the change in glycerol conversion and the yields of the reaction products during the reaction conducted in the presence of a platinum/zirconia catalyst (FIG. 4) and in the presence of a platinum/carbon catalyst (FIG. 5).
Figure 5:
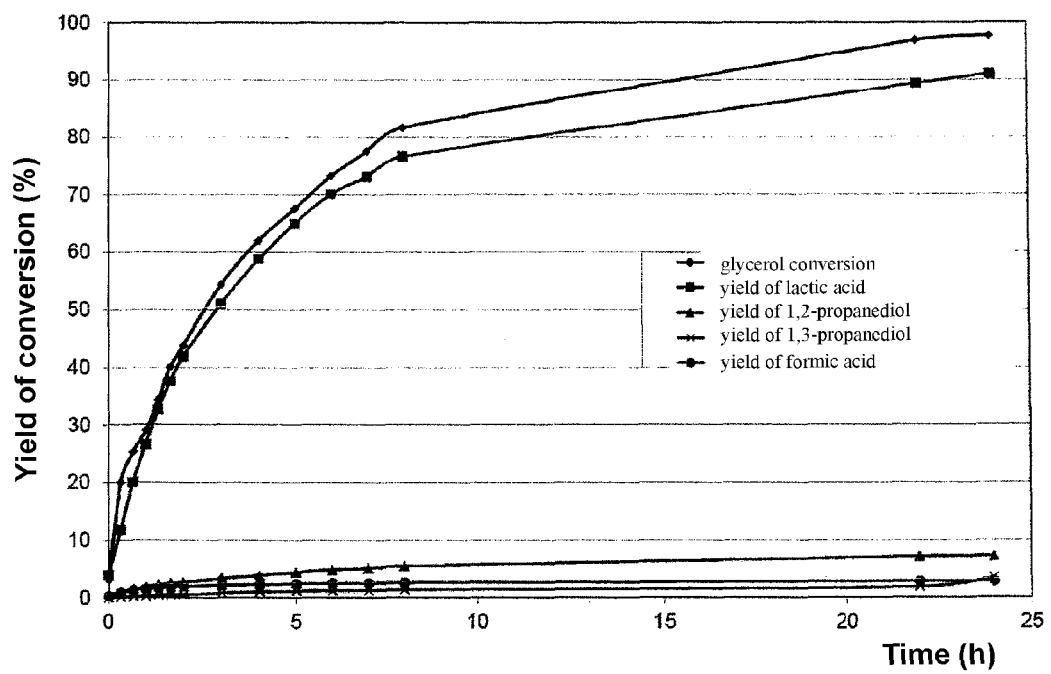

Synthesis of Lactic Acid According to the Method of the Invention and Impact of the Glycerol Concentration The impact of the initial glycerol concentration on the reaction according to the invention as described in Example 1 was studied. To this end, the glycerol conversion and the yields of products formed were determined by kinetic analysis for the reaction conducted in Example 1, with 5 mol % glycerol (reaction (a)), and for an identical reaction but conducted with 25% glycerol (reaction (b)). Both reactions were conducted with the same catalyst batch. For the first reaction (a), 100 mL of 5% glycerol were mixed with 1.1 equivalent of NaOH in the presence 500 mg of Pt/ZrO$_2$ (1 wt %). The reaction was conducted at 180° C. for 25 h at a helium pressure of 30 bar. For the second reaction (b), 100 mL of 25 mol % glycerol were mixed with 1.1 equivalent of NaOH in the presence 500 mg of Pt/ZrO$_2$ (1 wt %). The reaction was conducted at 180° C. for 25 h at a helium pressure of 30 bar. The NaOH/Gly ratio was kept constant by adding sodium hydroxide. The keys of FIGS. 4 and 5 are the same as those used for FIGS. 2 and 3.

We see that the change in conversion is similar for these glycerol rates, and is greater than 95%. However, it is noted, surprisingly, that the lactic acid selectivity is significantly improved with a 25% glycerol solution. It reaches 90% in fact, instead of 80% with a 5% glycerol solution. Furthermore, it should be noted that in this case, the final pH of the solution is maintained above 12, conditions which favour the lactic acid selectivity.

Example 4

Figure 6:
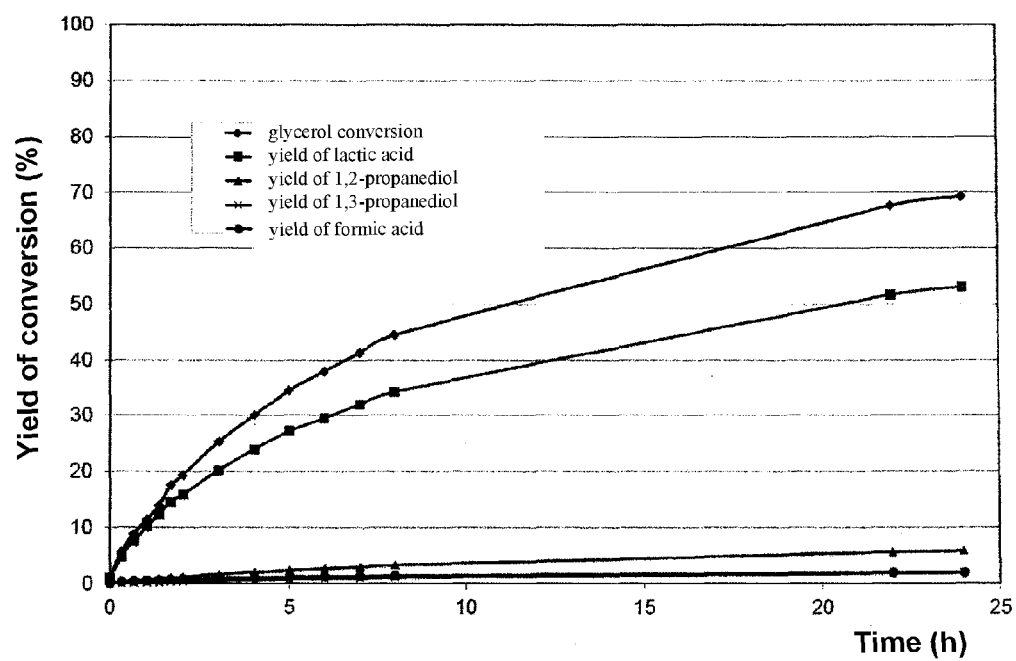
FIG. 6 shows the change in glycerol conversion and the yields of the reaction products during the reaction conducted in the presence of a platinum/zirconia catalyst from crude glycerol.

Synthesis of Lactic Acid According to the Method of the Invention for Various Starting Materials The impact of the glycerol source (purified or not (crude)) on the reaction according to the invention as described in Example 1 was studied. The glycerol conversion and the yields of products formed obtained in Example 1 were therefore compared with those obtained by kinetic analysis for a reaction conducted under the same reference conditions but with crude, unrefined glycerol. In this case, crude glycerol from the transesterification of rapeseed oil was obtained. This oil contained 83.84 wt % glycerol, 11.86 wt % water, 3.95 wt % ash, 0.33 w % various fats and 0.017% ethanol. The catalyst used is the Pt/ZrO$_2$ described in Example 1. For the reaction from crude glycerol, 100 mL of 5 mol % crude glycerol were mixed with 1.1 equivalent of NaOH in the presence of 500 mg of Pt/ZrO$_2$ (1 wt %). The reaction was conducted at 180° C. for 25 h at a helium pressure of 30 bar. The activity of Pt/ZrO$_2$ for the crude glycerol conversion is lower (see FIG. 6), with a decrease in glycerol conversion of about a factor of 2 (conversion at 5 h: 64% and 35%). However, the lactic acid selectivity remains similar (i.e. about 75%). The keys of FIG. 6 are the same as those used for FIGS. 2 to 5.

Example 5

Synthesis of Lactic Acid According to the Method of the Invention with Various Concentrations of NaOH and Temperatures The yields and selectivities of the lactic acid synthesis according to the invention as described in Example 1 were compared with those of reactions using different NaOH/glycerol ratios. 100 mL of a 5% glycerol solution were mixed in a stainless steel autoclave equipped with a Teflon® container, with 0 to 1.8 M of NaOH in the presence of 500 mg of 1% Pt/ZrO$_2$ catalyst. The reaction was conducted at an initial helium pressure of 15 bar for 24 h at temperatures of 180° C. and 220° C. The glycerol conversion, the yields of products formed as well as the initial and final pH values, and the carbon balance of the reaction were determined for all the following reactions. Two reactions were conducted at a temperature of 180° C.: the first in the presence of an equimolar NaOH/glycerol mixture (Table 2, entry 1) and the second in the presence of a slight excess of base corresponding to 1.1 equivalent of NaOH (Table 2, entry 2). The first reaction reaches a lactic acid selectivity of 69% for an 89% conversion rate (61% yield). The second reaction conducted in the presence of a slight excess of base reaches even better values in terms of conversion (95%) and lactic acid selectivity (74% yield). Four other reactions were conducted at a temperature of 220° C. with NaOH/glycerol ratios of 0 (Table 2, entry 3), 1.2 (Table 2, entry 4), 1 (Table 2, entry 5) and 1.8 (Table 2, entry 6). The conversion and selectivity of reaction (2) are similar to those of reaction (6), while using a smaller quantity of NaOH. The balance of carbon-containing products in solution is complete and no traces of CO$_2$ are detected in the gas phase. Selective hydrogenolysis of glycerol in lactic acid can therefore be conducted in the presence of a low NaOH/Gly ratio and 1% Pt/ZrO$_2$ catalyst.

Reaction (3) exhibits good conversion (74%) although the lactic acid selectivity is low, with a lactic acid yield of 9%. In this case, the majority products of the reaction are, in order, 1,2-PDO (41%) and hydroxyacetone (10%). Surprisingly, when the NaOH/Gly ratio is increased slightly from 0 to 0.2, the conversion decreases slightly (64%). At the same time, however, the AL selectivity increases from 12% to 38% and lactic acid becomes the majority product (4). Reactions (5) and (6) exhibit respective conversions of 99% and 100%, observed after 24 hours. These ratios can significantly increase the lactic acid yield, which reaches 65% and 70% respectively. Unexpectedly, however, reduced pH and temperature conditions produce the best results. It was observed that the increase in lactic acid selectivity with the NaOH/Gly ratio is accompanied by a steady increase in the proportion of hydrogen in the gas phase.

Irrespective of the NaOH/Gly ratio, the organic carbon balance in solution is never 100% at 220° C. These results suggest that at this temperature, reforming phenomena occur in aqueous phase.

TABLE 2

Influence of the NaOH/Glycerol ratio in the presence of 1% Pt/ZrO$_2$ catalyst

| No. | NaOH/Gly. (mol/mol) | T (° C.) | pHi | pHf | Conv. (%) | Carbon balance (%)[a] | AL[c] | Yield (%)[b] 1,2-PDO[c] | Others[c] |
|---|---|---|---|---|---|---|---|---|---|
| 1 | 1 | 180 | 12.9 | 9.5 | 89 | 99 | 61 | 10 | AF(5), EG(2), 1,3-PDO(2), AA(1) |
| 2 | 1.1 | 180 | 13.0 | 11.3 | 95 | 100 | 74 | 10 | AF(6), EG(3), 1,3-PDO(2), AA(1) |
| 3 | 0 | 220 | — | 3.2 | 74 | 89 | 9 | 41 | HA(10), EtOH(3), EG(2), AA(1), 1-PO(1) |
| 4 | 0.2 | 220 | 12.6 | 4.2 | 64 | 86 | 24 | 20 | HA(6), EtOH(3), EG(2), AA(1) |
| 5 | 1 | 220 | 13.1 | 8.9 | 100 | 91 | 65 | 6 | AF(6), EG (2), 1,3-PDO(2), AA(1) |
| 6 | 1.8 | 220 | 13.0 | 12.4 | 100 | 89 | 70 | 2 | AF (5), EtOH(1) 1,3-PDO(2), AA(2), |

[a]The carbon balance was determined by TOC analysis.
[b]Determined by HPLC.
[c]AL: lactic acid; 1,2-PDO: 1,2-propanediol; 1,3-PDO: 1,3-propanediol; AA: acetic acid; AF: formic acid; EG: ethylene glycol and EtOH: ethanol; HA: hydroxyacetone.

The invention is not limited to the embodiments described and other embodiments will be clearly apparent to those skilled in the art.

The invention claimed is:

1. A method for preparing lactic acid comprising a conversion step of converting glycerol in presence of a platinum-based heterogeneous catalyst on a zirconia-based support, the converting performed in a basic medium under inert atmosphere.

2. The method according to claim 1, wherein the platinum-based heterogeneous catalyst is a platinum on zirconia catalyst.

3. The method according to claim 1, wherein the basic medium comprises from 0.5 to 5 molar equivalents of a base with respect to glycerol.

4. The method according to claim 1, wherein the basic medium comprises a slight excess of base, in moles, with respect to glycerol.

5. The method according to claim 4, wherein the basic medium comprises from 1 to 1.2 molar equivalents of a base with respect to glycerol.

6. The method according to claim 1, wherein the basic medium is obtained by adding NaOH.

7. The method according to claim 6, wherein said conversion step is conducted under nitrogen pressure.

8. The method according to claim 1, wherein crude glycerol is used in the conversion step.

9. The method according to claim 1, wherein the quantity of glycerol used in the conversion step is at least 25% (moles) of starting materials.

10. The method according to claim 1, wherein the conversion step is partially conducted at a temperature from 170° C. to 250° C.

11. The method according to claim 8, wherein the crude glycerol comprises less than 85% by weight of glycerol.

12. The method according to claim 1, wherein the conversion step is conducted partially at a temperature from 170° C. to 180° C.

13. The method according to claim 1, wherein the conversion step is conducted partially at a temperature under 180° C.

14. The method according to claim 1, wherein the conversion step is conducted entirely at a temperature from 170° C. to 250° C.

15. The method according to claim 1, wherein the conversion step is conducted entirely at a temperature from 170° C. to 180° C.

16. The method according to claim 1, wherein the conversion step is conducted entirely at a temperature under 180° C.

* * * * *